US00PP27673P3

(12) United States Plant Patent
Danziger

(10) Patent No.: US PP27,673 P3
(45) Date of Patent: Feb. 14, 2017

(54) **NEW GUINEA *IMPATIENS* PLANT NAMED 'DHARSCLVDR'**

(50) Latin Name: *Impatiens hawkeri*
Varietal Denomination: DHARSCLVDR

(71) Applicant: Gavriel Danziger, Moshav Mishmar Hashiva (IL)

(72) Inventor: Gavriel Danziger, Moshav Mishmar Hashiva (IL)

(73) Assignee: Danziger 'DAN' Flower Farm (IL)

( * ) Notice: Subject to any disclaimer, the term of this patent is extended or adjusted under 35 U.S.C. 154(b) by 68 days.

(21) Appl. No.: 14/545,462

(22) Filed: May 7, 2015

(65) Prior Publication Data

US 2016/0330893 P1 Nov. 10, 2016

(51) Int. Cl.
*A01H 5/02* (2006.01)

(52) U.S. Cl.
USPC ..... Plt./318.6

(58) Field of Classification Search
USPC ..... Plt./317, 318, 318.6
See application file for complete search history.

*Primary Examiner* — Susan McCormick Ewoldt
*Assistant Examiner* — Karen Redden
(74) *Attorney, Agent, or Firm* — Cassandra Bright

(57) ABSTRACT

A new and distinct *Impatiens* cultivar named 'DHARSCLVDR' is disclosed, characterized by large lavender flowers, well branched plant form and good sun resistance. The new variety is an *Impatiens*, normally produced as an outdoor garden or container plant.

2 Drawing Sheets

Figure 1:
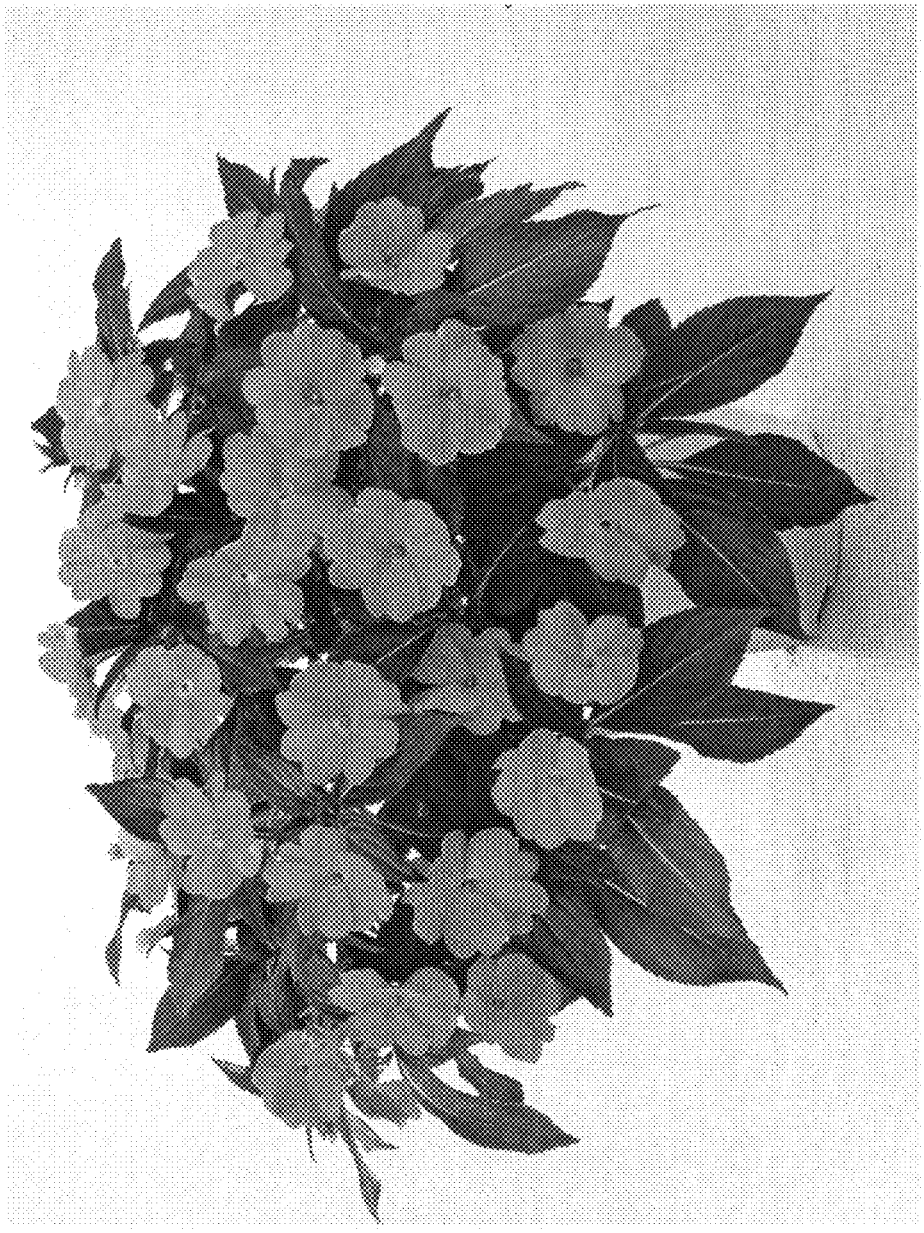

Latin name of the genus and species: *Impatiens hawkeri.* Variety denomination: 'DHARSCLVDR'.

BACKGROUND OF THE INVENTION

The new *Impatiens* cultivar is a product of a planned breeding program conducted by the inventor, Gavriel Danziger, in Moshav Mishmar Hashiva, Israel. The objective of the breeding program was to produce new *Impatiens* varieties for ornamental commercial applications. The cross resulting in this new variety was made during March of 2012.

The seed parent is the, unpatented, proprietary variety referred to as *Impatiens* 'BM-2847'. The pollen parent is the unpatented, propriety variety referred to as *Impatiens* 'BM-2899'. The new variety was discovered in December of 2012 by the inventor in a group of seedlings resulting from the 2012 crossing, in a research greenhouse in Moshav Mishmar Hashiva, Israel.

Asexual reproduction of the new cultivar was performed by leaf cuttings. The cuttings are from an apical bud that has no more than two expanded leaves and three to four immature leaves present. This was first performed at a research greenhouse in Moshav Mishmar Hashiva, Israel in January of 2013 and has shown that the unique features of this cultivar are stable and reproduced true to type in multiple successive generations.

SUMMARY OF THE INVENTION

The cultivar 'DHARSCLVDR' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'DHARSCLVDR' These characteristics in combination distinguish 'DHARSCLVDR' as a new and distinct *Impatiens* cultivar:

1. Large flowers.
2. Lavender flower color.
3. Good branching.
4. Sun resistant plant.

Plants of the new cultivar 'DHARSCLVDR' are similar to plants of the seed parent, *Impatiens* 'BM-2884' in most horticultural characteristics, however, plants of the new cultivar 'DHARSCLVDR' differ in the following;

1. 'DHARSCLVDR' has lavender flowers while the parent has white blush flowers.
2. Less plant vigor than the parent.

Plants of the new cultivar 'DHARSCLVDR' are similar to plants of the pollen parent, *Impatiens* 'BM-2899' in most horticultural characteristics, however, plants of the new cultivar 'DHARSCLVDR' differ in the following;

1. 'DHARSCLVDR' has lavender flowers while the parent has pink flowers.
2. The new variety has a lighter leaf color than the pollen parent.
3. The new variety has smaller flowers than the pollen parent.

COMMERCIAL COMPARISON

Plants of the new cultivar 'DHARSCLVDR' are comparable to the unpatented commercial variety *Impatiens* 'DHAR330'. The two *Impatiens* varieties are similar in most horticultural characteristics; however, plants of the new variety 'DHARSCLVDR' differ in the following:

1. 'DHARSCLVDR' has lavender flowers while the comparator has pink flowers.
2. Less vigor than this comparator.
3. More compact growth habit than the comparator.

Plants of the new cultivar 'DHARSCLVDR' can also be compared to the patented commercial variety *Impatiens* 'SAKIMP012', U.S. Plant Pat. No. 19,392. The two *Impatiens* varieties are similar in most horticultural characteristics; however, the new variety 'DHARSCLVDR' differs in the following:

1. Lighter flower color than 'SAKIMP012'.
2. Larger flowers than 'SAKIMP012'.
3. More compact growth habit than 'SAKIMP012'.

BRIEF DESCRIPTION OF THE PHOTOGRAPHS

The accompanying photograph in FIG. 1 illustrates in full color a typical plant of 'DHARSCLVDR' grown outdoors, in a 13 cm pot. Age of the plant photographed is approximately 14 weeks from a rooted cutting.

Figure 2:
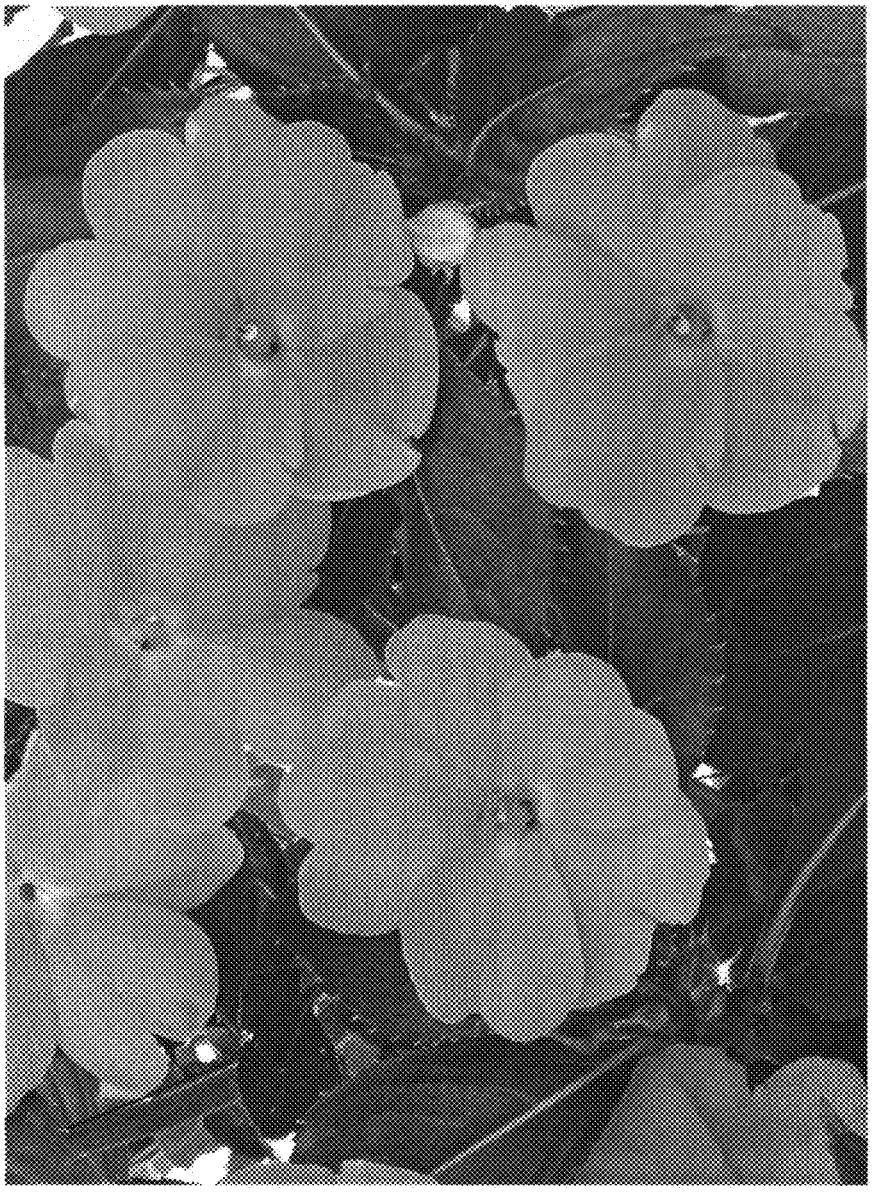

FIG. 2 illustrates a close up of the flowers. The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Mini Colour Chart 2001 except where general terms of ordinary dictionary significance are used. The following observations and measurements describe 'DHARSCLVDR' plants grown in the Autumn, in a greenhouse, in Moshav Mishmar Hashiva, Israel. The growing temperature ranged from 20° C. to 30° C. during the day and from 15° C. to 25° C. during the night. General light conditions are bright, normal sunlight. Measurements and numerical values represent averages of typical plant types.

Botanical classification: *Impatiens* 'DHARSCLVDR'

PROPAGATION

Type of propagation typically used: Cutting.
Time to initiate roots: 10-14 days Summer, 14-20 days Winter.
Root description: Fibrous adventitious roots.

PLANT

Age of plant described: Approximately 14 weeks.
Container size of the plant described: 13 cm.
Growth habit: Mounded.
Height: 25-30 cm.
Plant spread: 30-35 cm.
Growth rate: Medium.
Branching characteristics: Highly branched.
Quantity of primary lateral branches: 5-10.
Characteristics of primary lateral branches:
- *Quantity of primary lateral branches.*—5-8.
- *Form.*—Oval shape.
- *Length.*—15-20 cm.
- *Diameter.*—1 cm.
- *Color.*—RHS Yellow-green N144A.
- *Texture.*—Smooth.
- *Strength.*—Strong, very stable.

Internode length: 5-7 cm.

FOLIAGE

Leaf:
- *Arrangement.*—Alternate.
- *Quantity.*—Approximately 20-25 per branch.
- *Average length.*—9 cm.
- *Average width.*—4 cm.
- *Shape of blade.*—Oblanceolate.
- *Apex.*—Apiculate.
- *Base.*—Acuminate.
- *Margin.*—Ciliate.
- *Texture of top surface.*—Smooth.
- *Texture of bottom surface.*—Smooth.
- *Pubescence.*—None.
- *Aspect.*—45 degree angle of attachment, flat leaf.
- *Color.*—Young foliage upper side: Near RHS Green N137C. Young foliage under side: Near RHS Green 137D. Mature foliage upper side: Near RHS Green N137A. Mature foliage under side: Near RHS Green 137C.
- *Venation.*—Type: Pinnate. Venation color upper side: Near RHS Green 138D. Venation color under side: Near RHS Green 138B.
- *Petiole.*—Length: 1 cm. Diameter: 0.5 cm. Color: Near RHS Green 138D. Texture: Smooth.

FLOWER

Natural flowering season: Flowers at any day length. All year round in a greenhouse environment. Flowering is continuous from spring until fall in an outdoor garden in Israel.
Days to flowering from rooted cutting: 10 weeks.
Inflorescence and flower type and habit: Single flowers raised above the foliage. The corolla consists of five petals.
Rate of flower opening: 10 to 15 days from bud to fully opened flower.
Flower longevity on plant: 5-8 days.
Persistent or self-cleaning: Self-cleaning.
Bud:
- *Shape.*—Ovate.
- *Length.*—2 cm.
- *Diameter.*—1.5 cm.
- *Color.*—Near RHS Violet 84C.

Flower size:
- *Diameter.*—7 cm.
- *Depth.*—Approximately 6 cm including spur.

Petals:
- *Quantity.*—5.
- *Arrangement.*—Overlapping.
- *Length.*—4 cm.
- *Width.*—4 cm.
- *Shape.*—Obcordate.
- *Apex.*—Heart Shape.
- *Base.*—Acute.
- *Margin.*—Entire.
- *Texture, upper and lower surfaces.*—Smooth.
- *Color.*—When opening, upper surface: Near RHS Purple N78D. When opening, lower surface: Near RHS Purple 76B. Fully opened, upper surface: Near RHS Purple N78C. Fully opened, lower surface: Near RHS Violet 84C.

Spurs:
- *Quantity per flower.*—1.
- *Length.*—5 cm.
- *Diameter.*—0.1 cm.
- *Aspect.*—Spur curvature 40°-45° from peduncle.

*Color*.—Towards base: Near RHS Yellow-green 150D. Towards Apex: Near RHS Yellow-green 144C.

Sepals:

*Quantity*.—2.

*Length*.—1.5 cm.

*Width*.—1 cm.

*Shape* (*overall*).—Oblong. Apex: Caudate. Base: Rounded.

*Margin*.—Entire.

*Color*.—Near RHS Yellow-Green 144A.

Peduncles:

*Length*.—6 cm.

*Diameter*.—0.3 cm.

*Angle*.—About 45° to the lateral branch.

*Strength*.—Stable, flexible.

*Texture*.—Smooth.

*Color*.—Near RHS Yellow-Green 144D.

Fragrance: None.

REPRODUCTIVE ORGANS

Stamens: There are five stamens with anthers that are more or less fused and form a cap over the ovary.

*Number*.—5.

Anthers:

*Shape*.—Oblong.

*Length*.—Approximately 0.5 cm.

*Color*.—Near RHS Red-Purple 63B.

*Pollen*.—Color: Near RHS White 155D. Quantity: Few.

Pistil:

*Number:* 1.

*Length:* 0.5 cm.

*Style*.—Length: 0.5 cm. Color: Near RHS Yellow-Green 144A.

*Stigma*.—Shape: Round. Color: Near RHS White 155D. Ovary Color: Near RHS Yellow-Green 149D.

OTHER CHARACTERISTICS

Seeds and fruits: 5-10 seeds per fruit.

Disease/pest resistance: Neither resistance nor susceptibility to normal diseases and pests of *Impatiens* have been observed.

Temperature tolerance: Tolerant at 30° C. and tolerant at 5° C. degrees Celsius (grows best at 10° C.-28° C.).

What is claimed is:

1. A new and distinct cultivar of *Impatiens* plant named 'DHARSCLVDR' as herein illustrated and described.

* * * * *